United States Patent [19]
Hu et al.

[11] Patent Number: 6,091,840
[45] Date of Patent: *Jul. 18, 2000

[54] METHODS AND APPARATUS FOR SINGLE SLICE HELICAL IMAGE RECONSTRUCTION IN A COMPUTED TOMOGRAPHY SYSTEM

[75] Inventors: Hui Hu, Waukesha, Wis.; Yun Shen, Hino, Japan

[73] Assignee: General Electric Company, Milwaukee, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/754,242

[22] Filed: Nov. 20, 1996

Related U.S. Application Data

[63] Continuation-in-part of application No. 08/576,765, Dec. 21, 1995, Pat. No. 5,606,585.

[51] Int. Cl.[7] ........................................................ G06K 9/00
[52] U.S. Cl. .............................. 382/131; 378/15; 378/901
[58] Field of Search .............................. 382/131; 378/15, 378/901, 27; 600/425

[56] References Cited

U.S. PATENT DOCUMENTS

| | | | |
|---|---|---|---|
| 5,216,601 | 6/1993 | Crawford et al. | 378/14 |
| 5,270,923 | 12/1993 | King et al. | 382/131 |
| 5,513,236 | 4/1996 | Hu | 378/15 |
| 5,515,409 | 5/1996 | Hsieh | 378/15 |
| 5,606,585 | 2/1997 | Hu | 378/15 |

OTHER PUBLICATIONS

Bresler et al., "Optimal Interpolation in Helical Scan 3D Computerized Tomography." ICAS SP–89, vol. 3, pp. 1472–1475, May 1989.

Kudo et al. "Helical–Scan Computed Tomography Using Cone–beam Projections." 1991 IEEE Nuclear Science Symposium and Medical Imaging Conference, vol. 3, pp. 1958–1962, Nov. 1991.

*Primary Examiner*—Jon Chang
*Attorney, Agent, or Firm*—Armstrong Teasdale; Christian G. Cabou; Phyllis Y. Price

[57] ABSTRACT

The present invention, in one form, is a system for performing image reconstruction using data acquired from a single detector row in a helical scan. More specifically, a modified weighting factor $W_f(\beta,\gamma)$, which is a shifted and weighted average version of the single slice helical weighting factor, is generated. The modified weighting factor is then applied to data to reduce image noise and artifacts and/or increase image sharpness.

23 Claims, 1 Drawing Sheet

METHODS AND APPARATUS FOR SINGLE SLICE HELICAL IMAGE RECONSTRUCTION IN A COMPUTED TOMOGRAPHY SYSTEM

This application is a continuation-in-part of U.S. patent application Ser. No. 08/576,765, filed Dec. 21, 1995, now U.S. Pat. No. 5,606,585, issued Feb. 25, 1997.

FIELD OF THE INVENTION

This invention relates generally to computed tomography (CT) imaging and more particularly, to image reconstruction using data collected by a CT system in a single slice helical scan.

BACKGROUND OF THE INVENTION

In at least one known single slice CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon a one row array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed volume coverage is acquired. Such a system generates a single helix from a one fan beam helical scan. The helix mapped out by the fan beam yields projection data from which images in each prescribed slice may be reconstructed.

Reconstruction algorithms for helical scanning typically use helical weighting algorithms which weight the collected data as a function of view angle and detector channel index. Specifically, prior to filtered back projection, the data is weighted according to a helical weighting factor, which is a function of both the gantry angle and detector angle. Although the known algorithms generate compact slice profiles, some noticeable artifacts may be generated in the reconstructed image. Additional image quality issues with reconstructed images include a lack of "sharpness" in the image.

It would be desirable to provide an algorithm which facilitates reducing artifacts and increasing image "sharpness". It also would be desirable to provide an algorithm which offers reasonable trade-offs between artifact reduction and slice profile in helical image reconstruction. It further would be desirable to provide such an algorithm which does not significantly increase the processing time.

SUMMARY OF THE INVENTION

These and other objects may be attained in a CT system configured to perform a single slice helical scan, which includes a projection domain z filtering algorithm that generates a modified weighting factor. More particularly, and with respect to generating the modified weighting factor, a helical reconstruction algorithm weighting factor is shifted in the view angle direction and averaged to generate the modified weighting factor. Examples of image reconstruction algorithms which may be utilized in reconstructing an image from data obtained in a helical scan are described in Crawford and King, "Computed Tomography Scanning With Simultaneous Patient Translation", Med. Phys. 17(6), 967–982, 1990.

In one embodiment, the helical weighting factor is modified according to gantry angle ($\beta$), detector angle ($\gamma$), and a filter kernel (h(i)) in accordance with the following:

$$W_f(\beta, \gamma) = \sum_{i=-n}^{i=n} h(i) W(\beta - i\Delta\beta, \gamma)$$

where:

$\gamma$ is the detector angle;

$\beta$ is the gantry angle;

$W(\beta,\gamma)$ is the original weighting coefficient generated by the helical reconstruction algorithm;

$\Delta\beta$ is the shift along the view angle direction; and h(i) is the weighting applied to the i th shifted version. The filter kernel (h(i)) can be selected, as described hereinafter, to provide image smoothing, i.e., reduce noise and image artifacts, or to increase image "sharpness". The modified weighting factor is thus a shifted and weighted average version of the original weighting factor.

By modifying the weighting factor as described above, the reduced noise and artifacts, or increased image "sharpness", in a single slice helical image reconstruction may be achieved. Such algorithm also does not significantly increase the processing time and offers reasonable trade-offs between artifact reduction and slice profile.

DETAILED DESCRIPTION OF THE DRAWINGS

Figure 1:
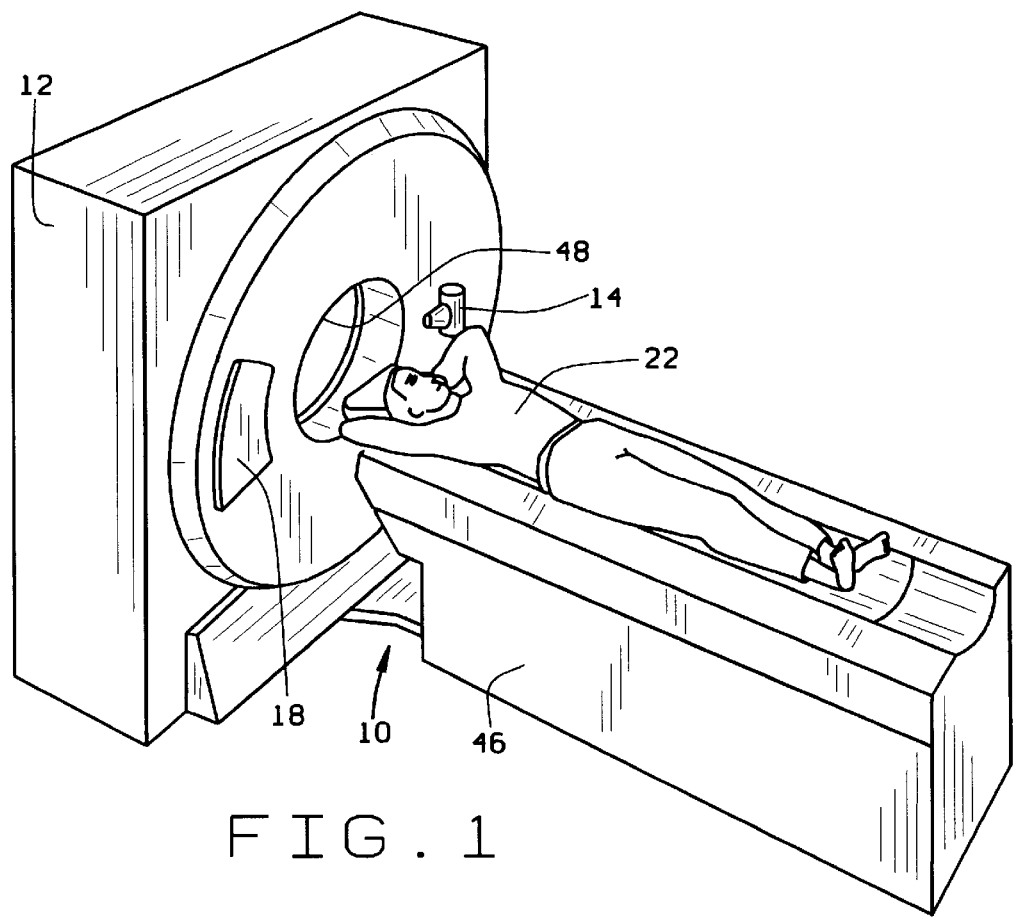
FIG. 1 is a pictorial view of a CT imaging system.
Figure 2:
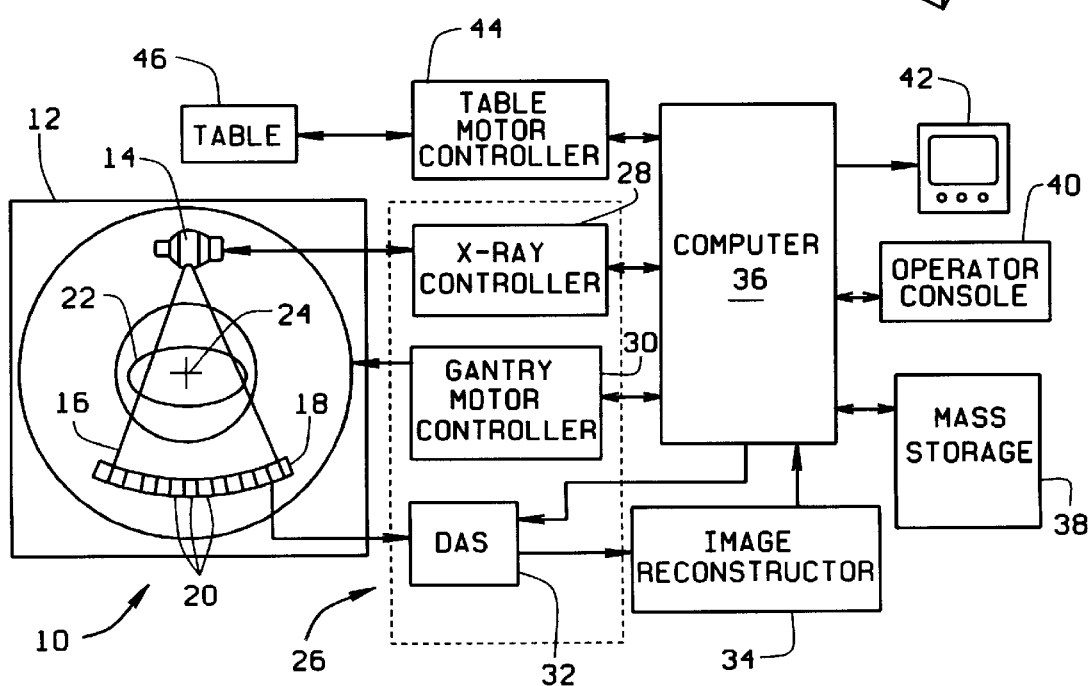
FIG. 2 is a block schematic diagram of the system illustrated in FIG. 1.

Referring to FIGS. 1 and 2, a single slice computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by one row of detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated display device 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The known helical reconstruction algorithms may generally be classified as Helical Extrapolative (HE) or Helical Interpolative (HI) algorithms. These algorithms typically apply a weighting factor to the projection data in order to reconstruct an image. This weighting factor is generally based on both the fan angle and view angle.

Each image generated with a helical reconstruction algorithm, as described above, corresponds to a two dimensional slice taken through patient 22. Each image typically includes projection data acquired during only one rotation of gantry 12, or $2\pi$ worth of data. As explained above, such generated images may have objectionable artifacts and noise, particularly at the beginning and end of a rotation, i.e., $\beta=0$ or $\beta=2\pi$.

The following discussion of a z filtering algorithm and its image quality sometimes refers specifically to projection data. The z filtering algorithm, however, is not limited to practice in connection with such projection data and may be used with image data. Moreover, the present weighting factor modification is not directed to any particular single slice helical image reconstruction algorithm. Rather, the present weighting factor modification may be used in conjunction with many different types of single slice helical weighting factors. Further, in one embodiment, the z filtering algorithm would be implemented in computer 36 and would process, for example, data stored in mass storage 38. Many other alternative implementations are, of course, possible.

As one specific example, in a single slice system with one row of detectors, a helical reconstruction algorithm to be applied to projection data during reconstruction includes a weighting factor $W(\beta,\gamma)$ accorded to each gantry angle ($\beta$) and detector angle ($\gamma$). In accordance with the present invention, the modified weighting factor $W_f(\beta,\gamma)$ is:

$$W_f(\beta, \gamma) = \sum_{i=-n}^{i=n} h(i) W(\beta - i\Delta\beta, \gamma)$$

where:
$\gamma$ is the detector angle;
$\beta$ is the gantry angle;
$W(\beta,\gamma)$ is the weighting coefficient, applied or pursuant to, a helical reconstruction algorithm;
$\Delta\beta$ is the shift along the view angle direction; and
$h(i)$ is the weighting applied to the i th shifted version.

This modified weighting factor $W_f(\beta,\gamma)$ is a shifted and weighted average version of the helical weighting function. The kernel length is $2n+1$ terms. In most cases, $n=1$, or 3 terms, is sufficient. The modified weighting factor $W_f(\beta,\gamma)$ is applied to the projection data to generate z-averaged slices. More than one rotation, i.e., more than $2\pi$, worth of data is used to generate the z-average slices. By utilizing more than one rotation worth of data, discontinuities can be "smoothed" without significantly increasing the slice width.

In known single slice helical reconstruction, the slice profiles and image noises of reconstructed images are primarily determined by x-ray collimation, the patient-feeding speed, the x-ray tube output, and the weighting function $W(\beta,\gamma)$. In the present invention, and in addition to the foregoing, the filter kernel h(i) also affects slice profiles and image noises. Particularly, if filter kernel h(i) is (1,1,1), then image artifacts and noise are reduced, i.e., the image is "smoothed". Alternatively, if filter kernel h(i) is (-1,3,-1) Laplacian, for example, then image "sharpness" is increased. Accordingly, by selecting the filter kernel h(i), tradeoffs between slice profile and image noise can be made.

The profile width of the resulting z-averaged slice is related to both the intrinsic slice profile, i.e., the original slice profile without any z filtering, and the filter kernel. The region of the filter kernel is represented by $2n\Delta\beta$. The detailed shape of the profile of the resulting slice is also affected by kernel h(i). Accordingly, and in contrast to known algorithms, the resulting slice profile width can be broader than the intrinsic slice profile width. Therefore, image noise is reduced. In addition, it is believed that the x-ray tube output required for satisfactory image generation may be reduced.

In accordance with one embodiment, n, $\Delta\beta$ and kernel h(i) are selected in the final stage of image quality evaluation. Accordingly, these values may be inserted by an operator at console 40 or may be stored in computer 36. More particularly, computer 36 is configured to prompt an operator to select and input values for n, $\Delta\beta$ and h(i) via console 40. In one embodiment, if the width of profile of the z-filtered slice will not be larger than twice the intrinsic width, then it is believed that $n \leq 5$ is sufficient to remove image artifacts resulting from helical scanning. The load for computing $W_f(\beta,\gamma)$ is only $(2n+1)t+(2n+1)$ multiples+2n additions, where t is the load for computing the original weighting function $W(\beta,\gamma)$.

The above described algorithm facilitates reducing noises and artifacts in single slice helical image reconstruction. Such algorithm also facilitates increasing image "sharpness". Further, such algorithm is not believed to significantly increase the processing time and offers reasonable trade-offs between noise and artifact reduction and slice profile.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used. Similarly, while the values on n, $\Delta\beta$ and h(i) are described herein as being selected as the final stage of image quality evaluation, any or all of these values may be pre-selected and stored in the computer. Moreover, while the description herein references z filtering in the projection domain, z filtering also may be performed in the image domain. Accordingly, the spirit and scope of the invention are to be limited only by the terms of the appended claims.

What is claimed is:

1. A system for producing a tomographic image using data acquired from a single detector row in a helical scan, said system comprising an x-ray source and a single slice detector array, a processor coupled to said detector array and configured to:

generate a helical weighting factor based on a gantry angle and a detector angle, generate a modified weighting factor based on the generated helical weighting factor by shifting the helical weighting factor in the view angle direction, and apply the modified weighting factor to the data;

wherein said modified weighting factor $W_f(\beta,\gamma)$ is:

$$W_f(\beta, \gamma) = \sum_{i=-n}^{i=n} h(i)W(\beta - i\Delta\beta, \gamma)$$

where:

$\gamma$ is the detector angle;

$\beta$ is the gantry angle;

$W(\beta,\gamma)$ is the helical weighting coefficient;

$\Delta\beta$ is the shift along the view angle direction; and h(i) is the weighting applied to the ith shifted version, and h(i) is (−1,3,−1).

2. A system in accordance with claim 1 further comprising an operator console and wherein said processor is further configured to prompt an operator to input values for n, $\Delta\beta$ and h(i).

3. A system in accordance with claim 1 wherein said modified weighting factor is applied to projection data.

4. A system in accordance with claim 1 wherein said modified weighting factor is applied to image data.

5. In a system for producing a tomographic image of an object using data acquired from a single slice detector having a single detector row, a processor configured to:

generate a modified weighting factor $W_f(\beta,\gamma)$ in accordance with:

$$W_f(\beta, \gamma) = \sum_{i=-n}^{i=n} h(i)W(\beta - i\Delta\beta, \gamma)$$

where:

$\gamma$ is the detector angle;

$\beta$ is the gantry angle;

$W(\beta,\gamma)$ is the helical weighting coefficient;

$\Delta\beta$ is the shift along the view angle direction; and h(i) is the weighting applied to the ith shifted version, and h(i) is (−1,3,−1); and apply the modified weighting factor to the data.

6. In a system in accordance with claim 5 wherein the system further includes an operator console, and wherein said processor is further configured to prompt an operator to input values for n, $\Delta\beta$ and h(i).

7. In a system in accordance with claim 5 wherein said modified weighting factor is applied to projection data.

8. In a system in accordance with claim 5 wherein said modified weighting factor is applied to image data.

9. A method for weighting data acquired from a single detector row from a single slice detector in a helical scan executed by a computed tomography system, said method comprising the steps of:

generating a helical weighting factor based on a gantry angle and a detector angle;

generating a modified weighting factor based on the generated helical weighting factor by shifting the helical weighting factor in the view angle direction; and applying the modified weighting factor to the data;

wherein said modified weighting factor $W_f(\beta,\gamma)$ is:

$$W_f(\beta, \gamma) = \sum_{i=-n}^{i=n} h(i)W(\beta - i\Delta\beta, \gamma)$$

where:

$\gamma$ is the detector angle;

$\beta$ is the gantry angle;

$W(\beta,\gamma)$ is the helical weighting coefficient;

$\Delta\beta$ is the shift along the view angle direction; and h(i) is the weighting applied to the ith shifted version, and h(i) is (−1,3,−1).

10. A method in accordance with claim 9 further comprising the step of prompting an operator to select values for n, $\Delta\beta$, and h(i).

11. A method in accordance with claim 9 wherein said modified weighting factor is applied to projection data.

12. A method in accordance with claim 9 wherein said modified weighting factor is applied to image data.

13. A system for producing a tomographic image using data acquired from a single detector row in a helical scan, said system comprising an x-ray source and a single slice detector array, a processor coupled to said detector array and configured to:

generate a helical weighting factor based on a gantry angle and a detector angle, generate a modified weighting factor based on the generated helical weighting factor by shifting the helical weighting factor in the view angle direction, and apply the modified weighting factor to the data;

wherein said modified weighting factor $W_f(\beta,\gamma)$ is:

$$W_f(\beta, \gamma) = \sum_{i=-n}^{i=n} h(i)W(\beta - i\Delta\beta, \gamma)$$

where:

$\gamma$ is the detector angle;

$\beta$ is the gantry angle;

$W(\beta,\gamma)$ is the helical weighting coefficient;

Δβ is the shift along the view angle direction; and h(i) is the weighting applied to the ith shifted version, and h(i) is a sharpening filter.

14. A system in accordance with claim 13 further comprising an operator console and wherein said processor is further configured to prompt an operator to input values for n, Δβ and h(i).

15. A system in accordance with claim 13 wherein said modified weighting factor is applied to projection data.

16. A system in accordance with claim 13 wherein said modified weighting factor is applied to image data.

17. A method for weighting data acquired from a single detector row from a single slice detector in a helical scan executed by a computed tomography system, said method comprising the steps of:

generating a helical weighting factor based on a gantry angle and a detector angle;

generating a modified weighting factor based on the generated helical weighting factor by shifting the helical weighting factor in the view angle direction; and applying the modified weighting factor to the data;

wherein said modified weighting factor $W_f(\beta,\gamma)$ is:

$$W_f(\beta, \gamma) = \sum_{i=-n}^{i=n} h(i) W(\beta - i\Delta\beta, \gamma)$$

where:

γ is the detector angle;

β is the gantry angle;

$W(\beta,\gamma)$ is the helical weighting coefficient;

Δβ is the shift along the view angle direction; and h(i) is the weighting applied to the ith shifted version, and h(i) is a sharpening filter.

18. A method in accordance with claim 17 further comprising the step of prompting an operator to select values for n, Δβ, and h(i).

19. A method in accordance with claim 17 wherein said modified weighting factor is applied to projection data.

20. A method in accordance with claim 17 wherein said modified weighting factor is applied to image data.

21. In a system for producing a tomographic image of an object using data acquired from a single slice detector having a single detector row, a processor configured to:

generate a modified weighting factor $W_f(\beta,\gamma)$ in accordance with:

$$W_f(\beta, \gamma) = \sum_{i=-n}^{i=n} h(i) W(\beta - i\Delta\beta, \gamma)$$

where:

γ is the detector angle;

β is the gantry angle;

$W(\beta,\gamma)$ is the helical weighting coefficient;

Δβ is the shift along the view angle direction; and h(i) is the weighting applied to the ith shifted version, and h(i) is a sharpening filter; and apply the modified weighting factor to the data.

22. In a system in accordance with claim 21 wherein said modified weighting factor is applied to projection data.

23. In a system in accordance with claim 21 wherein said modified weighting factor is applied to image data.

* * * * *